United States Patent [19]

Bonnefous

[11] Patent Number: 5,107,840

[45] Date of Patent: Apr. 28, 1992

[54] DEVICE FOR MEASURING AND DISPLAYING OF ULTRASONIC ECHOGRAPHY THE FLOW RATE OF A BLOOD FLOW AND THE DILATION OF THE ASSOCIATED VESSEL

[75] Inventor: Odile Bonnefous, Nogent, France

[73] Assignee: U.S. Philips Corporation, New York, N.Y.

[21] Appl. No.: 703,223

[22] Filed: May 20, 1991

[30] Foreign Application Priority Data

May 22, 1990 [FR] France .................... 9006361

[51] Int. Cl.$^5$ .............................................. A61B 8/02
[52] U.S. Cl. ............................ 128/661.08; 73/861.25
[58] Field of Search ................ 128/660.05, 661.08, 128/661.09, 661.10, 662.01; 73/861.25

[56] References Cited

U.S. PATENT DOCUMENTS

| | | | |
|---|---|---|---|
| 4,391,148 | 7/1983 | Sainz et al. ..................... | 128/662.01 |
| 4,476,874 | 10/1984 | Taenzer et al. ................. | 128/660.05 |
| 4,630,612 | 12/1986 | Uchida et al. .................. | 128/661.09 |
| 4,757,822 | 7/1988 | DiGiuliomaria et al. ...... | 128/661.08 |
| 4,803,990 | 2/1989 | Bonnefous et al. ............ | 128/661.08 |
| 4,850,366 | 7/1989 | Ito et al. ......................... | 128/661.08 |
| 4,866,613 | 9/1989 | Amemiya et al. .............. | 128/661.08 |

Primary Examiner—Francis Jaworski
Assistant Examiner—George Manuel
Attorney, Agent, or Firm—William Squire

[57] ABSTRACT

The blood flow rate Q(t) is obtained from a first unit (300) measuring the speed V(t, z), z being the depth of examination, independent of the frequency of the ultrasonic wave used. In a similar manner a second measuring unit (500) enables the measurement of the radial speeds $V_1(t, z)$ and $V_2(t, z)$ of the shift of the two corresponding vessel walls, and thereafter, on account of two spatial integrations (606, 607) and time integrations (608, 609), the measurement of the instantaneous variation of the radius of the vessel $\Delta r(t)$. The functions Q(t) and $\Delta r(t)$ are thereafter displayed in several manners, for the purpose of comparison, for the duration of at least one cardiac cycle.

14 Claims, 3 Drawing Sheets

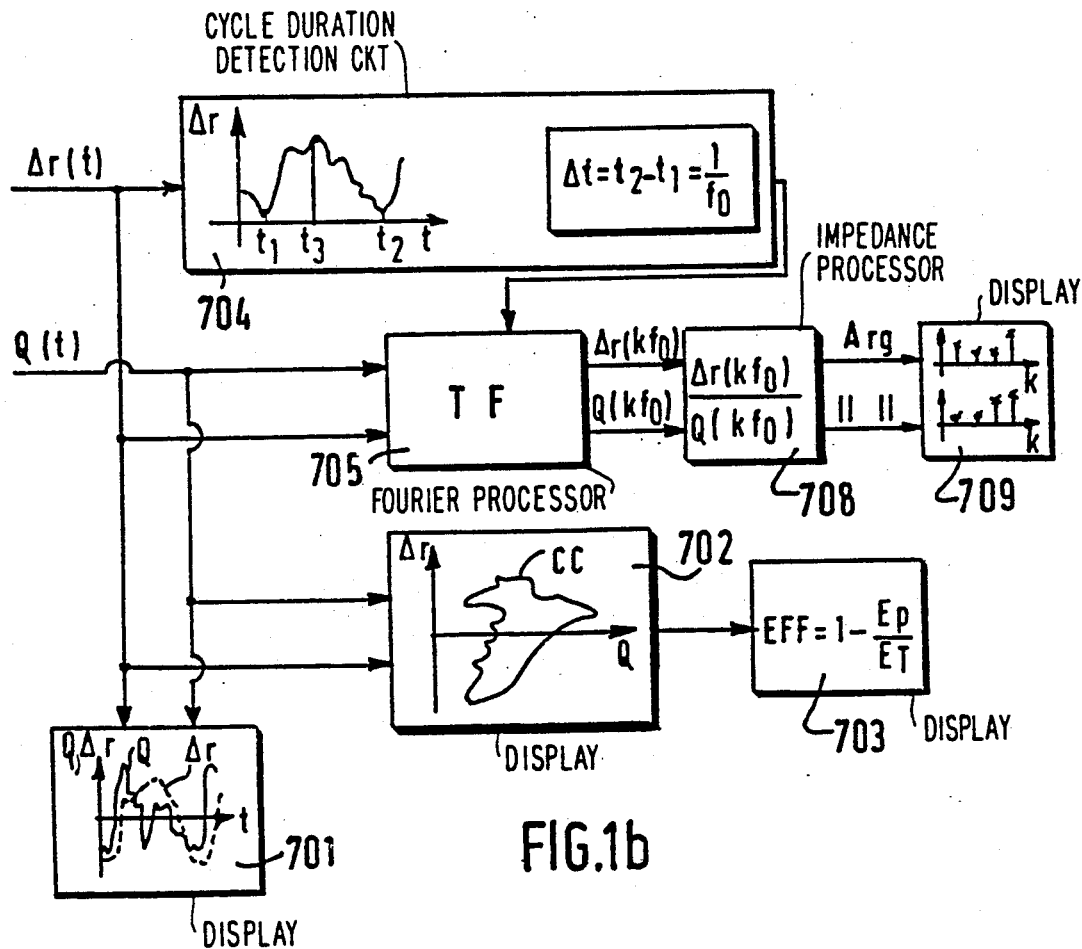
FIG.1b
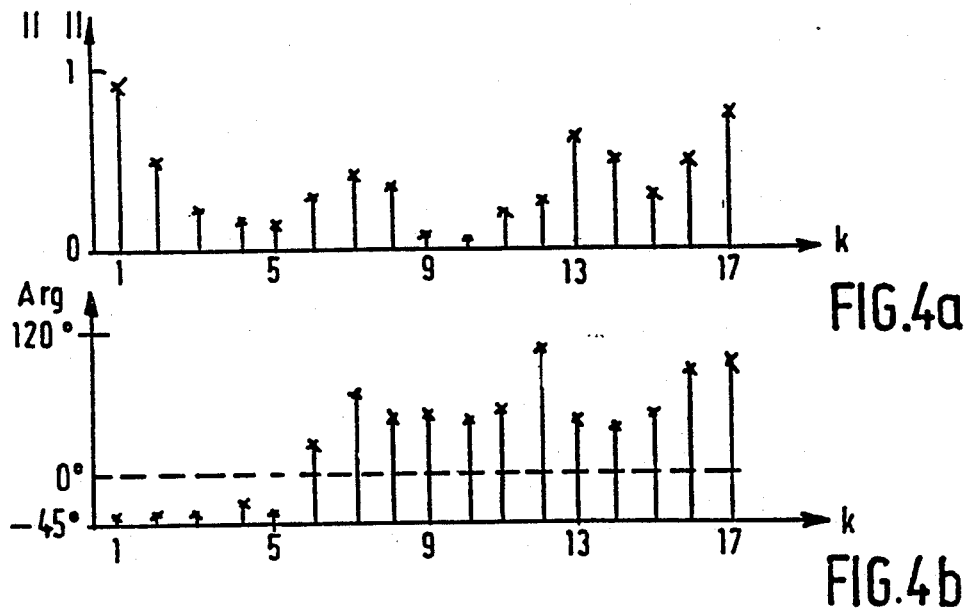
FIG.4a
FIG.4b

DEVICE FOR MEASURING AND DISPLAYING OF ULTRASONIC ECHOGRAPHY THE FLOW RATE OF A BLOOD FLOW AND THE DILATION OF THE ASSOCIATED VESSEL

The present invention relates to a device for measuring and displaying physiological parameters of a blood flow in a vessel, comprising a first measuring unit for ultrasonic echography of the speed $V(t,z)$ of the blood flow versus the time t and the depth of examination z, the measurement of the speed $V(t,z)$ being independent of the frequency of the ultrasound wave used, and comprising a memory for storing the speed samples $V(t,z)$.

The invention is used with great advantage in the general field of echographic exploration of blood flows in the blood vessels, and more specifically in the field of measuring and displaying, for diagnostic purposes, of characteristic physiological parameters of said flows.

Of interest is commonly owned copending application Ser. No. 619,274 entitled "Device for Measurement and Display of Physical Parameters of a Blood Flow by Ultrasonic echography" filed Nov. 28, 1990 in the same of O. Bonnefous.

BACKGROUND OF THE INVENTION

The clinical study by ultrasonic echography of blood flows is actually realized with apparatus which utilize the Doppler effect which takes into account the frequency difference, denoted Doppler frequency $f_D$, between the wave transmitted by a piezoelectric transducer and the wave received after interaction with the flow considered. The speed V of the blood flow is linked to $f_D$ by the relation:

$$f_D = 2(V/C)f_E \cos\theta$$

$f_E$ being the frequency of the transmitted ultrasound wave, $\theta$ being the angle between the ultrasound beam and the direction of the flow, and C the speed at which the sound travels.

The known Doppler devices render it more particularly possible for medical practitioners to have to interesting parameters, such as speed spectograms which show the distribution of the speed of flow V as a function of the time t. Nevertheless, the result obtained has a certain inaccuracy which is inherently linked to the basic principle of the method and which results from the fact that the frequency $f_E$ transmitted by the piezoelectric transducer has a certain distribution which has repercussions on the speed V via the above-mentioned relation (1).

Therefore, the technical problem to be solved by the present invention is to provide a device for measuring and displaying physiological parameters of a blood flow, as defined in the opening paragraph, which renders it possible to obtain, in addition to a more precise speed spectogram, the determination of additional physiological parameters with the desired precision, which so far have been unaccessible.

Amongst the devices capable of giving a speed measurement independently of the ultrasound frequency, there are those devices which function on the temporal correlation principle described in European Patent Application No. 0 225 667, and whose unit for measuring the flow speed includes an intercorrelation circuit which from two consecutive echoes supplies values of the correlation function, and a multiplexing-interpolating circuit which from the values of the correlation functions produce an estimate of the speed $V(t,z)$.

The precision obtained in the measurement of the flow speed renders it possible to provide, in addition to the display of the blood flow in mode M, for example, and the representation of the speed spectogram, the calculation of further physiological parameters which so far have been inaccessible by the conventional Doppler system because of their poor resolution at deeper levels.

SUMMARY OF THE INVENTION

Due to the precision thus obtained with a device according to an embodiment of the present invention the disadvantages of the prior art are mitigated and obviated to measuring and display device in the opening in the opening according to the present invention includes a combination of first means for determining the instantaneous flow rate $Q(t)$ from the samples of the speed $V(t, z)$ and second means for measuring the radial speeds $V_1(t,z)$ and $V_2(t,z)$ of the shift of the two walls of the vessel diametrically bounding the blood flow, means for storing the values of the speeds $V_1(t,z)$ and $V_2(t,z)$, third means comprising means for determining the local energy from which the fixed echoes $E_2(t,z)$ have not been removed, means for determining the respective thicknesses $d_1 = z_4 - z_3$ and $d_2 = z_6 - z_5$ of the walls, constituted by a threshold detector means of the value $E'_o$ for the determination of the values $z_3$, $z_4$, $z_5$, $z_6$, means for determining the respective vales $_1(t_0)$ and $_2(t_0)$ of the walls for each time value $t_0$ giving $1\ 2(t_0)$ $\Sigma_{d1}V_1(t,z)$ (or $\Sigma_{d2}V_2(t,z)$, respectively), means for dividing the mean values by $M_1$ (or $M_2$, respectively), $M_1$ and $M_2$ being the number of measuring samples of the segment $[z_3, z_4]$(or $[z_5, z_6]$, respectively), means for determining the shift of each wall, for generating a signal having the value $$D_1(t) = \Sigma_t V_1(t_0) \text{ and } D_2(t) = \Sigma_t V_2(t_0),$$

and means for determining the symmetrical shift of the walls, including subtraction means and divider means for producing as time samples the variation of the instantaneous radius of the vessel manifesting the value $\Delta r(t) = (D_2(t) - D_1(t))/2$ and means for displaying curves $Q(t)$ and $\Delta r(t)$ as a function of the time t.

Among the parameters which can be determined with an adequate precision by means of the present invention there are the mean speed $\hat{V}(t)$ and the instantaneous flow rate $Q(t)$ of the blood flow in a blood vessel and also the respective mean speeds $\hat{V}_1(t_0)$ and $\hat{V}_2(t_0)$ of the walls of the vessel, these latter two rendering it possible, after integration relative to time, to obtain the law of displacement of each wall, $D_1(t)$ and $D_2(t)$. From these displacements the variation of the instantaneous radius of the vessel $\Delta r(t)$ is derived and it is important to note that the function $\Delta r(t)$ is in a linear relation to the variation in the instantaneous pressure of the blood in the vessel $\Delta p(t)$. The simultaneous knowledge of the flow rate and the pressure renders it possible to effect several calculations and is suitable for several representations which are highly useful for the medical practitioner.

A preferred embodiment of the measuring and display device in accordance with the invention, is one wherein the first means for determining the instantaneous flow rate $Q(t)$ comprise a means for calculating the local energy from which the fixed echoes $E(t,z)$ have been removed, followed by a means for determining the diameter of the blood flow $D(t)=z_2(t)-z_1(t)$ constituted by threshold detector means having a value $E_0$, $z_2(t)$ and $z_1(t)$ being defined by $E(t, z_1(t))=E(t, z_2(t))=E_o$ means for determining the mean rate (t) of the blood flow formed by an adder producing $\Sigma_D V(t,z)$ and by a divide-by-M divider, M being the number of measuring samples of the segment $[z_1, z_2]$, and a means for calculating the flow rate Q(t) including means for calculating the gravity center $z_0(t)$ of the flow, formed an adder means giving $\Sigma_D V(t,z)z$ and a divider means for dividing by the mean rate (t) and adder means producing $\Sigma_D V(t,z)|z-z_0|$ followed by a multiple means for multiplying by a constant A which is a function of the angel $\theta$ between the flow and the ultrasound beam.

A particularly interesting mode of representation of the flow rate and the pressure variation, these two phenomena being combined, is in calculating and displaying the curve of the cardiac cycle, parametered versus time, comprising the points obtained by plotting on the ordinate the values-samples of the function $\Delta r(t)$ and on the abscissa the values-samples of the function of the instantaneous flow rate Q(t).

From there it is more in particular possible to derive, from the measurement of the surface of the cycle and of the surface subtended by the cycle, the calculation of the cardiac efficiency for the slice of the axial thickness dx of the analyzed vessel.

A further preferred embodiment of the measuring and display device in accordance with the invention which compatible with the preceding embodiments, is further includes a device for detecting the abscissa of a minimum, at the instant $t_1$, of a subsequent maximum at the instant $t_3$, and of a second subsequent minimum at the instant $t_2$, of the function $\Delta r(t)$, the duration $\Delta t = t_2 - t_1$ being the duration of a cardiac cycle, a Fourier series decomposition processor which receives the time-sampled signals $\Delta r(t)$ and $Q(t)$ between the instants $t_1$ and $t_2$ and derives therefrom the frequency samples $\Delta r(kf_0)$ and $Q(kf_0)$, $f_0 = 1/\Delta t$ being the basic frequency of the cardiac cycle and k being the order of the harmonic under consideration, and an impedance calculating processor which, for each harmonic, supplies the amplitude $\Delta r_k/Q_k$ and the phase $Arg(\Delta r_k/Q_k)$ of the impedance of the section of the analyzed vessel.

Means for displaying the amplitude and the phase of the impedance point-by-point, for each harmonic of the cycle allow an adequate characterization of this impedance.

It should be noted that the measurement and displays of the physiological parameters of a blood flow in a vessel described above are obtained without the aid of one or a plurality of catheters (or intravenous probes) that is without traumatism for the patient nor risks of obtaining false measurements by the observation apparatus itself.

The following description which is given by way of non-limitative example with reference to the accompanying drawings will make it better understood how the invention can be put into effect.

BRIEF DESCRIPTION OF THE DRAWING

FIGS. 1a and 1b in combination form the basic circuit diagram of a measuring and display device in accordance with an embodiment the invention.

FIGS. 4a and 4b show, for the first harmonics of the cardiac cycle, the amplitude and the phase of the impedance in the region of the analyzed vessel, respectively.

DESCRIPTION OF THE PREFERRED EMBODIMENT

Figure 1A:
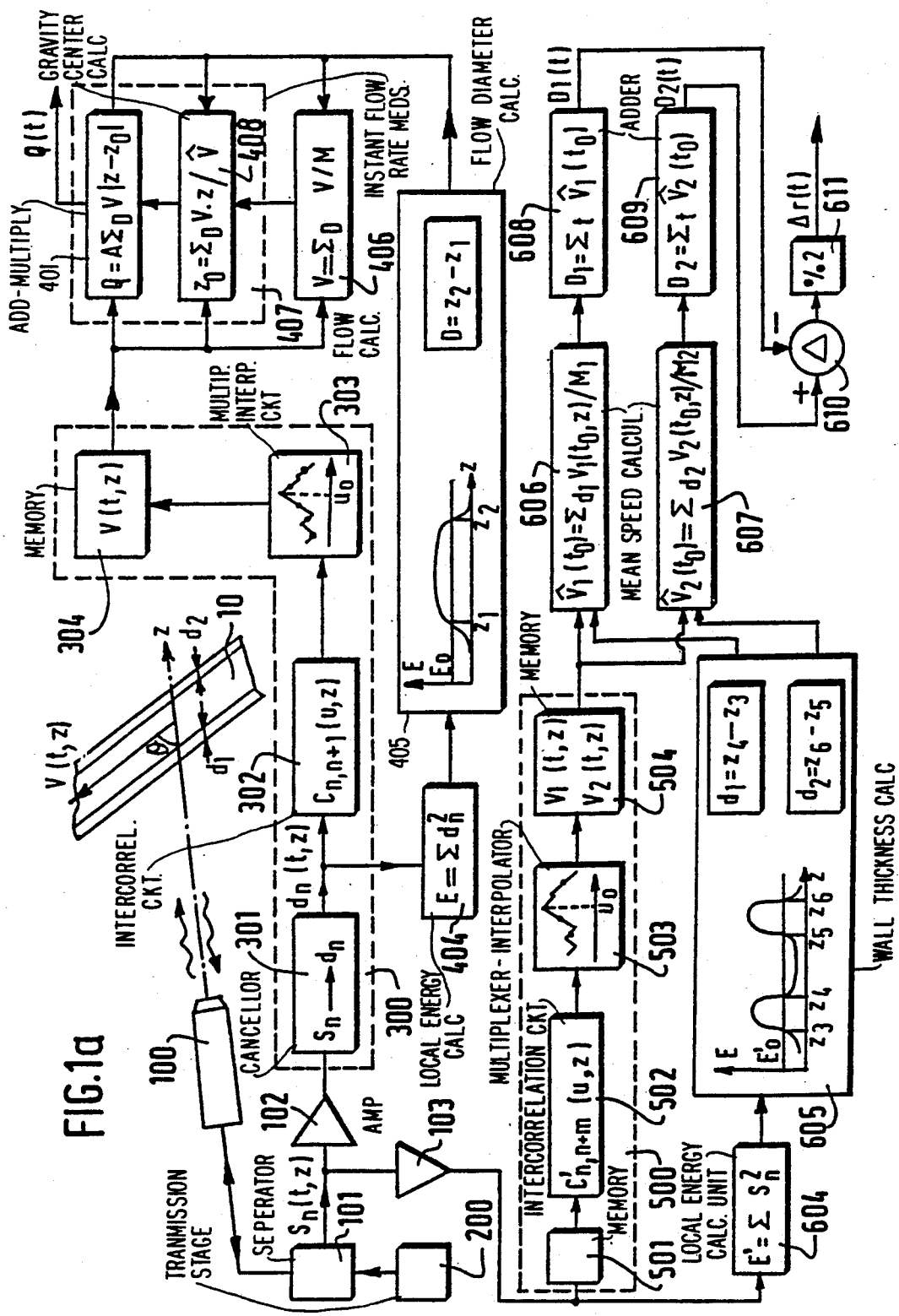

The circuit diagram of FIG. 1a shows a device for measuring physiological parameters of a blood flow 10. This device comprises a piezoelectric transducer 100 which may, for example, be a multi-element array. A transmission stage 200 connected to the transducer 100 provides the formation of an exploring ultrasonic beam whilst a first measuring unit 300 processes the echographical signals sent towards the transducer 100 so as to supply an estimate of the flow speed V(t,z) versus the time t and the depth of exploration z.

In a conventional manner, the transmission stage 200 comprises a sequencer formed by an oscillator and a frequency divider which at the chosen repetition rate 1/T controls a generator whose electric energizing signals are conveyed towards the transducer 100 which converts them into periodical ultrasonic pulse train signals. A separator 101 separating the transmission stage 200 and the measuring stage 300 is inserted between the transducer 100 and the stages 200, 300 and prevents overloading of the measuring circuit by the transmission signals.

The measuring unit 300 for measuring the speed V(t,z) shown in FIG. 1 includes a canceller 301 for the fixed echoes, in two points, for example, which supplies from the received signal $S_n(t, z)$ after amplification by an amplifier 102 a signal $d_n(t, z)$ from which its fixed components caused by specular reflections from the walls of the examined blood vessel are removed. The signal $d_n(t, z)$ originating from the fixed echo canceller 301 is thereafter processed in accordance with the so-called intercorrelation method described in the European Patent Application No. 0 225 667 corresponding to U.S. Pat. No. 4,803,990, which makes use of the fact that the ultrasonic signals retransmitted by a moving target are linked by the following equation:

$$d_{n+1}(t) = d_n(t-\tau)$$

which means that the signal $n+1$ is the replica of the preceding signal n but for a time shift $\tau$. The latter represents the additional time required for the ultrasonic wave for passing through the transducer-target-transducer path, from one shot to the other. Put differently:

$$\tau = 2VT/C$$

wherein V is the speed of the target and C the speed of sound. It will be obvious that a measurement of $\tau$ renders it possible to measure the speed V looked for.

The intercorrelation function between $d_n(t)$ and $d_{n+1}(t)$ defined by:

$$C_{n,n+1}(to,u) = \int_{to}^{to+W} d_{n+1}(t+u) d_n(t) dt$$

verifies:

$$C_{n,n+1}(to, u) = C_{n,n}(to, u-\tau).$$

The time to is connected with the depth of exploration z by to $=2z/C$, and W is the width of the integration window.

The function $C_{un}(to, u)$ is an autocorrelation function. and, because of this fact, is at its maximum for $u=o$. Thus, a measurement of the time shift $\tau$, and consequently of the speed V, can be effected by searching for which parameter u the function $C_{n,n+1}(to, u)$ is at its maximum. To that effect, the intercorrelation is sampled, with a sampling step $\Delta t$, between $u_{min} = -I\Delta t$ and $u_{max} = I\Delta t$ in steps of one unit so as to obtain $2I+1$ correlation function values. The maximum value of these $2I+1$ values corresponding to $u=uo$ allow the measurement of $\tau$ by using the equality $\tau = uo$. The calculation of the correlation functions is performed by the intercorrelation circuit 302 shown in FIG. 1.

In order to obviate errors inherent to the sampling operation in the determination of the maximum of the correlation function, it is possible to use a multiplexing-interpolation circuit 303 which from the values of the correlation functions supplies a more accurate estimate of the speed and the value of the corresponding correlation peak. The European Patent Application No. 0 225 667 gives an example of this type of echographical signal processing in which the correlation between signals is a "1-bit" correlation in the sense that the signals $d_{n+1}$ and $d_n$ employed previously are reduced to the sign of the ultrasonic signal. It is known that in this case, the peak of the correlation function is in the form of an isosceles triangle. The knowledge of this shape renders it possible to depart from the highest point and its two neighbouring points for a complete reconstruction, by linear interpolation, of the correlation peak and conseuently to determine with precision the location of uo.

In contrast to the conventional Doppler velocimeters, the flow rate $V(t,z)$ thus determined has the advantage that it is insensitive to the frequency dispersion of the ultrasonic wave utilized, which enables a much more complete exploitation of the results.

The values found for the speed $V(t,z)$ are stored in a storage memory 304 with a view to subsequent processing operations.

FIG. 1a shows how certain physiological parameters which are characteristic of the blood flow can be calculated. It refers first of all to the diameter $D(t)$ of the flow the measurement of which activates, at the output of the fixed echo canceller 301, a local energy calculation circuit 404:

$$\Sigma d^2_n (t,z)$$

and a circuit 405 for calculating the flow diameter
$D(t) = z_2(t) - z_1(t)$ constituted by a threshold detector having an adjustable value Eo, $z_1(t)$ and $z_2(t)$ being defined by
$E(t, z_1(t)) = E(t, z_2(t)) = Eo$.

Knowing, at each instant t, the diameter $D(t)$ of the blood flow, it is possible to calculate the average velocity (t) of the blood flow with a circuit 406 formed by an adder supplying $\tau_D V(t,z)$ and by a divide-by-M divider, M being the number of samples of the speed $V(t,z)$ utilized for the segment $[z_1, z_2]$.

Similarly, the instantaneous flow rate $Q(t)$ can be measured by a circuit 407 which, includes a circuit 408 for calculating the gravity center $z_0(t) = \Sigma_D V(t,z)z/ (t)$, constituted by an adder supplying $\Sigma_D V(t, z)z$ and a divider dividing by the means rate (t) calculated by the circuit 406, and, an adder 401 supplying $\Sigma_D V(t,z)z - z_0$ followed by a multiplier (not shown) multiplying by the constant $A = \pi \cos\theta/\sin^2\theta$, $\theta$ being the angle between the blood flow and the ultrasonic beam.

A further physiological parameter to be measured with precision, necessary for putting the invention into effect is the instantaneous blood pressure variation $\Delta p(t)$ inside the analyzed vessel. In known manner, by virtue of the elastic behavior of the walls of the vessel, the function $\Delta p(t)$ is linked to the variation of the instantaneous radius of the vessel, $\Delta r(t)$ by the relation: $\Delta p(t) = K\Delta r(t)$, K being a constant for the section of the analysed vessel. This constant depends on both the mechanical characteristics (elasticity) of the vessel and the angle $\theta$. For the measurement of $\Delta r(t)$, a second measuring unit 500 for measuring the radical speeds $V_1(t,z)$ and $V_2(t,z)$ of the shift of the two walls of the vessel which diametrically bound the blood flow as well as further storage and calculating circuits as shown at the bottom of FIG. 1a.

The signal $S_n(t,z)$ at the output of the separator 101 is applied, via an amplifier 103 to the measuring unit 500. Amplification by the amplifier 103 is less than the amplification by the amplifier 102 so as to match the dynamic of the echo signals on the walls of the vessel to the calculation stages provided downstream. This circumstance is associated with the fact that the second measuring unit does not include a fixed echo canceller since these echo signals from the wall are the signals dealt with at present. In the measuring unit 500, the signal $S_n(t,z)$ supplied by the amplifier 103 is first stored in a memory 501 and thereafter processed in accordance with the intercorrelation method described in the European Patent application No. 0 225 667, in a manner similar to the manner described in the foregoing for unit 300. However, the processing repetition rate can advantageously be chosen as a multiple M of the transmission repetition period T. Actually, the displacement speeds of the walls being very low, typically equal to 0.5 cm/s, preference should be given to the correlation of consecutive signals which are farther apart (by n shots) in time and consequently are not adjacent to each other. The corresponding correlation operation, in block 502, may be represented in the form: Cn, $n+m(u,z)$. In order to remove errors inherent to the sampling operation in the determination of the maximum of the correlation function, a multiplexing-interpolating circuit 503 can be used. The values found for the speeds $V_1(t,z)$ and $V_2(t,z)$ are stored in a memory 504 with a view to their subsequent processing.

FIG. 1a shows how further characteristics parameters of the vessel can be calculated, ending with the calculation of the function $\Delta r(t)$. Measured first is the thickness of the walls $D_1(t)$ and $D_2(t)$ which are diametrically opposite each other and whose measurement triggers, at the output of the amplifier 103 a circuit 604 for calculating the local energy $E'(t,z) = \tau_n S_n'(t,z)$ and a circuit 605 for calculating the thicknesses of the walls $D_1(t) = z_4(t) - z_3(t)$ and $d_2(t) = z_6(t) - z_5(t)$ formed by a threshold detector having an adjustable value $E'_0$. To avoid any ambiguity as regards the location of the walls, it is possible to display on a screen, not shown, an image of the examined vessel, in accordance with the "mode M" representation, of the development in the course of the time of the speed profile of the vessel walls and to provide that the user which possesses a light pen (mouse) selects on the screen a point within each wall, from which point onwards the subsequent adding operations (integrations) can be effected, towards the terminals $z_3$ and $z_4$, or $z_5$ and $z_6$, respectively. Encoding the speed in the M mode is the coding operation utilized in the CFM (Color Flow Mapping) systems: for example red encodes one direction of shift, blue the opposite direction and the intensity of the speed is encoded by the intensity of the color.

Knowing, at each instant $t_0$, the thicknesses $d_1(t)$ and $d_2(t)$ of the walls, it is possible to calculate the mean speeds $_1(t_0)$ and $_2(t_0)$ of the walls with circuits 606 and 607 which are each formed by an adder and a divider which supply respectively:

$$V_1(t_0) = \Sigma_{d1} V_1(t_0, Z)/M_1$$

$$V_2(t_0) = \Sigma_{d2} V_2(t_0, Z)/M_2$$

$M_1$ and $M_2$ being the number of measuring samples from the segment $[z_3-z_4]$, and $[z_5-z_6]$, respectively.

A second integration (summing of the samples) in time of the average speed, renders it possible to obtain with precision the displacement function of each wall, which is effected by the adders 608 and 609:

$$D_1(t) = \sum_{t_0=0}^{t_0=t} V_1(t_0)$$

$$D_2(t) = \sum_{t_0=0}^{t_0=t} V_2(t_0)$$

It should be noted that the speeds of the walls, perpendicular to the rates of flow of the blood flow, are very low, of the order of 0.5 cm/s. On the other hand one wants to extract only the motions in opposite directions of the walls, that is to the motions which are symmetrical relative to the center of the vessel. Therefore, the motions of the walls in the same direction are to be eliminated, that is to the motions which are anti-symmetrical due to either an unbalance of the pressure forces on each side of the vessel, or to slight movements of the transducer. The mean symmetrical displacement is obtained by subtracting $D_2(t)-D_1(t)$ in a subtractor 610 followed by a division by two by means of a divider 611 which supplies the variation of the instantaneous radius $\Delta r(t)$:

$$\Delta r(t) = \tfrac{1}{2}(D_2(t) - D_1(t)).$$

FIG. 1b which forms the sequel of the circuit diagram of FIG. 1a shows the use of the simultaneous supply of the physiological parameters Q(t) and $\Delta r(t)$, available for the practitioner. This use consists in the display, which preferably is effected simultaneously on a single screen (not shown) forming the display means.

Figure 2:
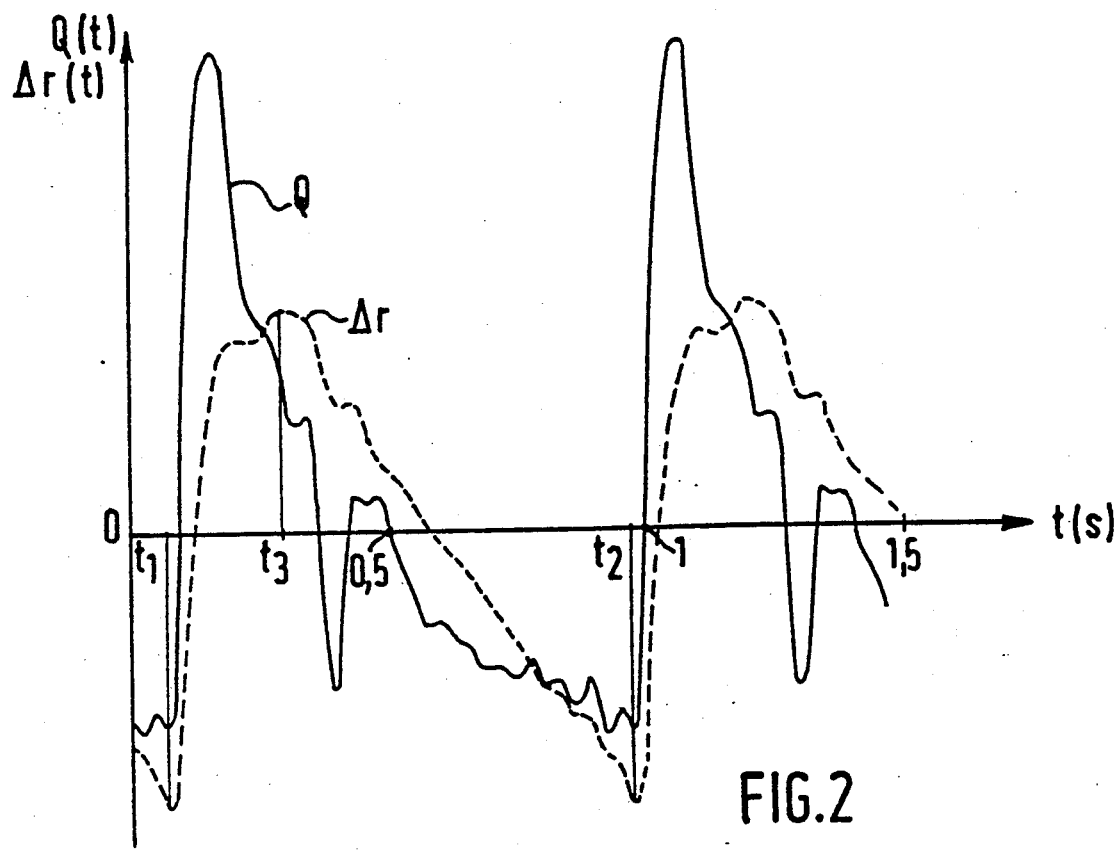
FIG. 2 shows the flow rate Q(t) and radius variation $\Delta r(t)$ functions which characterize the blood flow versus time.

In the first place, the curves Q and $\Delta r$ are plotted versus the time t along the same coordinate axis in the block 701 (FIG. 1b) and in FIG. 2, the flow rate Q being shown as a solid line and the variation of the radius $\Delta r$ by a broken line. The curves obtained are of course periodical curves, at the rate of the cardiac cycle. This cycle can be designated relative to the abscissa of the minimum and the maximum of the function $\Delta r(t)$ for example. In FIG. 2 in which the d.c. component has been removed from the curves $\Delta r$ and Q to facilitate their comparison, two consecutive minima are shown, at the instants $t_1$ and $t_2$ and a maximum inserted between these two minima, at the instant $t_3$.

Figure 3:
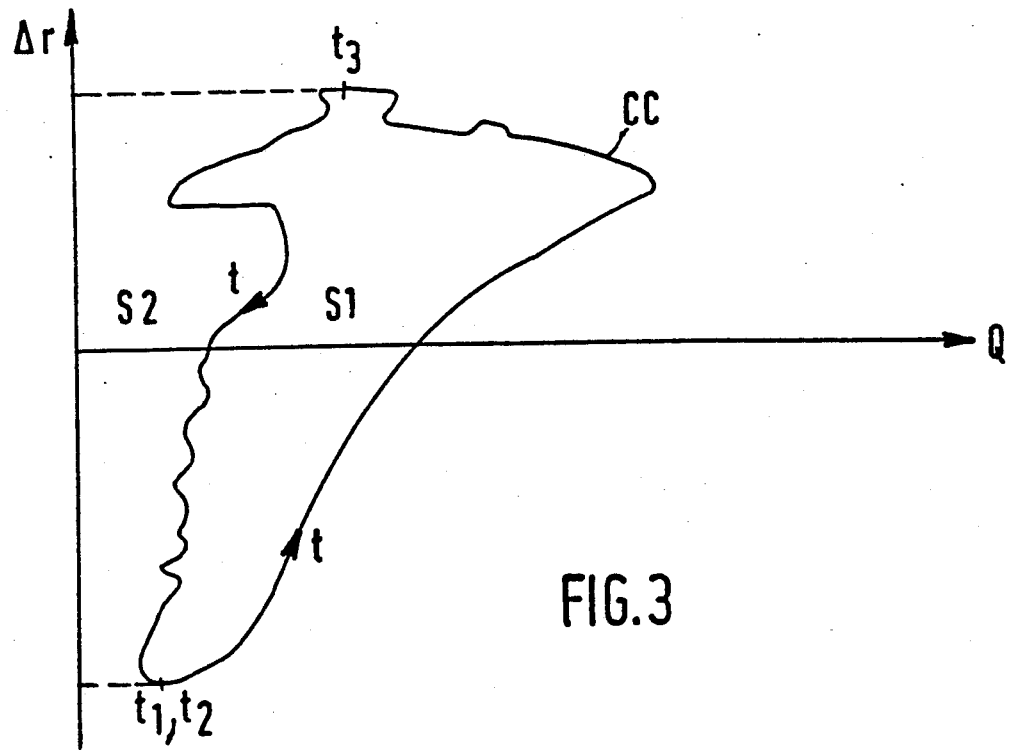
FIG. 3 shows a cardiac cycle such as it is shown in the region of the analyzed blood vessel.

In hook 702, FIG. 1b and in FIG. 3 the curve CC of the cardiac cycle is displayed, parametered in time, formed by the points obtained by plotting at the ordinates the values of the function $\Delta r(t)$ and at the abscissa the values of the function of the instantaneous flow rate Q(t), the curve Q being shown with the actually measured values. The intermingled minima obtained at the instants $t_1$ and $t_2$ and the maximum obtained at the instant $t_3$ are denoted on the curve CC. While the value of the flow rate is here a measure of the real value of the blood flow in the analysed vessel, it should be noted that the function $\Delta r(t)$ relative to the displacement of the walls is in a linear relation with the variation of the instantaneous pressure, that is to say defined but for a multiplicative constant in conformity with the aforementioned relation: $\Delta p = K \Delta r$. This is in this case not disturbing for the medical practitioner, since the shape of the cardiac cycle can in itself yield useful information to the practitioner on any abnormalities this cycle may show. This is also not harmful for a determination of the efficiency of the cycle. It can actually be seen that the value of the boundary of curve CC of the overall cycle boundary is proportional to the losses by viscosity, $E_p$, for the slice of the analyzed vessel, wherein the total energy $E_T$ (kinetic energy of the blood) is given in the same proportion by the integral of this curve between the instants $t_1$ and $t_3$, i.e. the boundary values $S_1+S_2$, $S_2$ being the adjacent boundaries subtended by the cycle towards the ordinate axis. The efficiency of the vessel (of the artery) during the duration of the cardiac cycle, EFF, can then be defined by:

$$EFF = \frac{E_T - E_p}{E_T} = 1 - \frac{E_p}{E_T}$$

and is displayed on the screen, in block 703.

On a mathematical plane, the integrals to be calculated can be expressed, but for a multiplicative coefficient which does not occur in the calculation of EFF, by:

$$\int_{t_1}^{t_2} Q(t)\, d\Delta r(t) \text{ for } E_p$$

and:

$$\int_{t_1}^{t_3} Q(t)\, d\Delta r(t), \text{ for } E_T.$$

The efficiency EFF can also be defined as the ratio between the remaining kinetic energy and the total energy furnished for the analysed vessel portion, during a cycle, and then depends on the robustness and/or the local constriction of the vessel wall.

The upper portion of the circuit diagram of FIG. 1b and FIGS. 4a and 4b illustrate the impedance calculation performed on the blood flow which may be derived from the periodic functions Q(t) and $\Delta r(t)$. This impedance can be defined as the ratio between the pressure and the flow rate p(t)/Q(t). Here the pressure and consequently the impedance is obtained but for a multiplicative constant. A detection circuit for detecting two consecutive minima of the function $\Delta r(t)$, circuit 704, is provided which furnishes the duration of the cycle $t_2-t_1=\Delta t = 1/f_0$, $f_0$ being the fundamental frequency of the cycle. The data $f_0$ is applied to a processor for the Fourier series decomposition TF, 705, which moreover receives the time-sampled signals $\Delta r(t)$ and Q(t) and, by time-frequency transformation, converts them into frequency samples having complex values Δr(kf₀) and Q(kf₀), k being the order of the harmonic considered relative to the fundamental frequency f₀. These frequency samples are thereafter applied to an impedance calculating processor 708 which, by dividing the complex numbers, supplies for each harmonic, the normalized amplitude $\|\Delta r_k/Q_k\|$ and the phase $\text{Arg}(\Delta r_k/Q_k)$ of the impedance of the analyzed vessel section. These normalized amplitudes and these phases are displayed by display means 709, shown in greater detail in FIGS. 4a and 4b in which the order k of the harmonics up to the 17th harmonics are shown at the abscissa.

It should be noted that in block 702, FIG. 1b, it is possible to illustrate sequentially in a manner not shown, the cardiac cycle for each harmonic considered, each curve thus obtained, parametered in time as the curve CC, assumming the form of an ellipse. It is also possible to deduce the energic contribution caused by each harmonic of the cardiac cycle.

What is claimed is:

1. An ultrasonic echography device employing ultrasound waves having fixed echoes $E_2(t,z)$ manifesting stationary objects for measuring and displaying physiological parameters of blood flow in a vessel whose walls shift in position, said device for measuring the speed $V(t,z)$ of blood flow versus time t and depth z of examination into a body containing the vessel, the measurement of speed $V(t,z)$ being independent of the frequency of said ultrasound waves, said device comprising:

first memory means for storing speed samples $V(t,z)$ of said flow;

means responsive to said stored speed samples for generating a first signal manifesting the instantaneous flow rate $Q(t)$ from said samples;

means responsive to said waves for measuring radial speeds $V_1(t,z)$ and $V_2(t,z)$ of a shift of the vessel walls diametrically bounding said blood flow;

second memory means for storing the values of measured speeds $V_1(t,z)$ and $V_2(t,z)$;

first means for determining local energy $E'(t,z)$ from said waves including said fixed echoes;

means responsive to said determined local energy for determining the respective thicknesses $d_1 = z_4 - z_3$ and $d_2 = z_6 - z_5$ of the walls including threshold detector means for determining the values $z_3, z_4, z_5$ and $z_6$ from the value of $E'_o$ where $E'_o$ is a threshold local energy value of said determined local energy;

means for determining the respective mean speed values $_1(t_o)$ and $_2(t_o)$ of the walls for each value of $t_o$;

means responsive to said determined mean speed values for providing signals representing the sums $\Sigma_{d1}V_1(t,z)$ and $\Sigma_{d2}V_2(t,z)$, respectively, and for dividing said sums by $M_1$ and $M_2$, respectively, $M_1$ and $M_2$ being the number of measuring samples of the segments $[z_3, z_4]$ and $[z_5, z_6]$, respectively;

means for determining the shift of each said walls producing respective signals having the values $D_1(t) = \Sigma_1(t_o)$ and $D_2(t) = \Sigma_2(t_o)$;

means for determining a symmetrical shift of the walls including substraction means and divide means for producing signals in the form of time samples the variation of the instantaneous radius value $\Delta r(t) = (D_2(t) - D_1(t))/2$ of said vessel; and means for displaying curves represented y the values of the signals $Q(t)$ and $\Delta r(t)$ as a function of time.

2. A measuring and display as claimed in claim 1 further including means for displaying the curve of a cardiac cycle CC, parametered in time, formed by points obtained by plotting in the ordinate direction the values of the function $\Delta r(t)$ in a linear relationship with the variation of the instantaneous pressure in the vessel and int he abscissa direction those values of the function of said instantaneous flow rate $Q(t)$.

3. A measuring and display device as claimed in claim 2, including means responsive to said instantaneous flow rate value for calculating the cardiac efficiency EFF defined by:

$$EFF = 1 - E_p/E_t$$

in which relation $E_p$ is the boundary $S_1$ of the cardiac cycle and $E_t$ is the boundary of the cycle increased by the adjacent boundary $S_2$ subtended by the cycle boundary in the ordinate direction.

4. A measuring and display device as claimed in claim 1 furthermore includes a device for detecting the abscissas of a minimum at the instant $t_1$, of a subsequent measurement; at the instant $t_3$ and of a second subsequent minimum, at the instant $t_2$, of the function $\Delta r(t)$, the duration $\Delta t = t_2 - t_1$ being the duration of a cardiac cycle, a Fourier-series decomposing processor which receives the time-sampled signals $\Delta r(t)$ and $Q(t)$ between the instants $t_1$ and $t_2$ and derives therefrom frequency samples $\Delta r(kf_o)$ and $Q(kf_o)$, $f_o = 1/\Delta t$ being the fundamental frequency of the cardiac cycle and k the order of the harmonics considered, and an impedance calculating processor which, for each harmonic, furnishes the amplitude $\Delta r_k/Q_k$ and the phase $\text{Arg}(\Delta r_k/Q_k)$ of the impedance of the analysed vessel section.

5. A measuring and display device as claimed in claim 4 further including means for displaying the amplitude and the phase of the impedance point-by-point, for each harmonic of the cardiac cycle.

6. A measuring and display device as claimed in claim 1, wherein said means for generating the first signal and the means for measuring the radial speeds of the shift of the walls each comprises intercorrelation means for supplying, from two consecutive echos, values of correlation functions, and a multiplexing-interpolating means for furnishing from said correlation values an estimate of the speed $V(t, z)$, or $V_1(t, z)$ and $V_2(t, z)$, respectively.

7. A measuring and display device as claimed in claim 1 including means for removing the fixed echos $E(t, z)$ from said waves wherein said first means for generating said first signal includes second means for determining from said waves local energy from which the fixed echoes $E(t, z)$ have been removed, means responsive to the second means determined local energy for determining the diameter of the blood flow $D(t) = z_2(t) - z_1(t)$ including second threshold detector means for detecting the value $E_0$, $z_2(t)$ and $z_1(t)$ defined by:

$$E(t, z_1(t)) = E(t, z_2(t)) = E_0,$$

means for determining the average rate $V(t)$ of the flow for producing a signal having the value:

$$\Sigma_d V(t, z)/M$$

M being the number of measuring samples of the segment $[Z_1, Z_2]$, and means for determining the flow rate $Q(t)$ comprising means for determining the center of gravity $z_0(t)$ of the blood flow including means producing a signal $\Sigma_D V(t, z)z$ and divider means for dividing the latter signal value by the average rate (t) and means for producing a signal of value:

$$\Sigma_D V(t, z)|z-z_0|$$

said latter means including multiplier means responsive to said latter signal for multiplying that signal value by a constant value A which is a function of the angle $\theta$ between the blood flow and the ultrasonic beam.

8. A measuring and display device as claimed in claim 7 further including means for displaying the curve of a cardiac cycle CC, parametered in time, formed by points obtained by plotting in the ordinate direction the values of the function $\Delta r(t)$ in a linear relationship with the variation of the instantaneous pressure in the vessel and in the abscissa direction those values of the function of said instantaneous flow rate Q(t).

9. A measuring and display device as claimed in claim 8 including means responsive to said instantaneous flow rate value for calculating the cardiac efficiency EFF defined by:

$$EFF = 1 - E_p/E_t$$

in which relation $E_p$ is the boundary $S_1$ of the cardiac cycle and $E_t$ is the boundary of the cycle increased by the adjacent boundary $S_2$ subtended by the cycle boundary in the direction of the ordinate axis.

10. A measuring and display device as claimed in claim 9 wherein the function $\Delta r(t)$ has a maximum value occurring at instant $t_3$ between first and second minimum values occurring in respective successive instances $t_1$ and $t_2$, said device further including means for detecting the instant $t_1$, the subsequently occurring instant $t_3$ and the subsequently occurring instant $t_2$ of the function $\Delta r(t)$, the duration $\Delta t = t_2 - t_1$ being the duration of a cardiac cycle, Fourier-series decomposing processor means which receives the time-sampled signals $\Delta r(t)$ and Q(t) between the instants $t_1$ and $t_2$ and derives therefrom frequency samples $\Delta r(kf_0)$ and $Q(kf_0)$, $f_0 - 1/\Delta t$ being the fundamental frequency of the cardiac cycle and k the order of the harmonics considered, and impedance calculating processor means which, for each harmonic, furnishes the amplitude $\Delta r_k/Q_k$ and the phase $Arg(\Delta r_k/Q_k)$ of the impedance of the analyzed vessel section.

11. A measuring and display device as claimed in claim 10 further including means for displaying the amplitude and the phase of the impedance, for each harmonic of the cardiac cycle.

12. A measuring and display device as claimed in claim 11 wherein said means for generating the first signal and the means for measuring the radial speeds of the shift of the walls each comprise intercorrelation means for supplying, from two consecutive echos, values of the correlation functions, and a multiplexing interpolating means for furnishing from said correlation values an estimate of the speed V(t, z), or $V_1(t, z)$ and $V_2(t, z)$, respectively.

13. A measuring and display device as claimed in claim 8 wherein the function $\Delta r(t)$ has a maximum value occurring at instant $t_3$ between first and second minimum value occurring in respective successive instance $t_1$ and $t_2$, said device further including means for detecting the instant $t_1$, the subsequently occurring instant $t_3$ and the subsequently occurring instant $t_2$ of the function $\Delta r(t)$, the duration $\Delta t = t_2 - t_1$ being the duration of a cardiac cycle, Fourier-series decomposing processor means which receives the time-sampled signals $\Delta r(t)$ and Q(t) between the instants $t_1$ and $t_2$ and derives therefrom frequency samples $\Delta r(kf_0)$ and $Q(kf_0)$, $f_0 - 1/\Delta t$ being the fundamental frequency of the cardiac cycle and k the order of the harmonics considered, and impedance calculating processor means which, for each harmonic, furnishes the amplitude $\Delta r_k/Q_k$ and the phase $Arg(\Delta r_k/Q_k)$ of the impedance of the analyzed vessel section.

14. A measuring and display device as claimed in claim 7 wherein the function $\Delta r(t)$ has a maximum value occurring at instant $t_3$ between first and second minimum values occurring in respective successive instances $t_1$ and $t_2$, said device further including means for detecting the instant $t_1$, the subsequently occurring instant $t_3$ and the subsequently occurring instant $t_2$, of the function $\Delta r(t)$, the duration $\Delta t = t_2 - t_1$ being the duration of a cardiac cycle, Fourier-series decomposing processor means which receives the time-sampled signals $\Delta r(t)$ and Q(t) between the instants $t_1$ and $t_2$ and derives therefrom frequency samples $\Delta r(kf_0)$ and $Q(kf_0)$, $f_0 - 1/\Delta t$ being the fundamental frequency of the cardiac cycle and k the order of the harmonics considered, and impedance calculating processor means which, for each harmonic, furnishes the amplitude $\Delta r_k/Q_k$ and the phase $Arg(\Delta r_k/Q_k)$ of the impedance of the analyzed vessel section.

* * * * *